(12) United States Patent
Will et al.

(10) Patent No.: US 10,119,161 B2
(45) Date of Patent: Nov. 6, 2018

(54) METHODS AND KITS FOR JOINING FRAGMENTED NUCLEIC ACIDS TOGETHER

(71) Applicant: Roche Molecular Systems, Inc., Pleasanton, CA (US)

(72) Inventors: Stephen G. Will, Oakland, CA (US); Yuker Wang, Palo Alto, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 191 days.

(21) Appl. No.: 14/965,343

(22) Filed: Dec. 10, 2015

(65) Prior Publication Data

US 2017/0166953 A1    Jun. 15, 2017

(51) Int. Cl.
  *C12Q 1/68*  (2018.01)
  *C12P 19/34* (2006.01)
  *C12Q 1/686* (2018.01)

(52) U.S. Cl.
  CPC ........ *C12Q 1/686* (2013.01); *C12Q 2531/113* (2013.01); *C12Q 2533/10* (2013.01); *C12Q 2537/101* (2013.01); *C12Q 2537/143* (2013.01)

(58) Field of Classification Search
  None
  See application file for complete search history.

(56) References Cited

PUBLICATIONS

Heckman et al., "Gene splicing and mutagenesis by PCR-driven overlap extension", Nature Protocol, vol. 2, No. 4, pp. 924-932. (Year: 2007).*
Didenko, V.V., "DNA Probes Using Fluorescence Resonance Energy Transfer (FRET): Designs and Applications," Biotechniques, vol. 31, No. 5, pp. 1106-1121. (Year: 2001).*
Giglio et al., "Demonstration of preferential binding of SYBR Green I to specific DNA fragments in real-time multiplex PCR", Nucleic Acids Research, vol. 31, No. 22, e136, pp. 1-5. (Year: 2003).*
Prodromou et al. (Protein Engineering, vol. 5, No. 8, pp. 827-829. (Year: 1992).*
Lin et al., Anal Biochem., 395(2):265-267 (2009).
Suzuki et al., Clinica Chimica Acta, 387, 55-58 (2008).
Perkel, BioTechniques, 56(1):12-14 (2014).
Castellanos-Rizaldos, E., et al., Enhanced Ratio of Signals Enables Digital Mutation Scanning for Rare Allele Detection, The Journal of Molecular Diagnostics, May 1, 2015, pp. 284-292, vol. 17, No. 3, Elsevier Inc.
Dahse, R., et al., PCR-based Testing for Therapy-related EGFR Mutations in Patients with Non-small Cell Lung Cancer, Anticancer Research, Jan. 1, 2008, pp. 2265-2270, vol. 28.

(Continued)

*Primary Examiner* — Young J Kim
(74) *Attorney, Agent, or Firm* — David J. Chang; M. Reza Savari (57) ABSTRACT

Methods and kits for joining fragmented nucleic acid sequences together are provided, including performing an amplifying step including contacting a sample suspected of including a fragmented target nucleic acid with a pair of external primers and a pair of self-complementary internal primers, and generating a full length target nucleic acid. The methods can include performing an amplifying step, a hybridizing step, and a detecting step. Furthermore, kits are provided that are designed for the detection of a target nucleic acid sequence.

7 Claims, 7 Drawing Sheets

(56) References Cited

PUBLICATIONS

Heckman, K.L., et al., Gene splicing and mutagenesis by PCR-driven overlap extension, Nature Protocols, Apr. 1, 2007, pp. 924-932, vol. 2, No. 4, Nature Publishing Group.
International Search Report dated Feb. 24, 2017 in Application No. PCT/EP2016/080225, 12 pages.
Rychlik, W., Selection of Primers for Polymerase Chain Reaction, Molecular Biotechnology, Jan. 1, 1995, pp. 129-134, vol. 3, No. 2, Humana Press Inc.
Suzuki, N., et al., Characterization of circulating DNA in healthy human plasma, Clinica Chimica Acta, Sep. 8, 2007, pp. 55-58, vol. 387, No. 1, Elsevier B.V.
Yuan, H., et al., A Modified Extraction Method of Circulating Free DNA for Epidermal Growth Factor Receptor Mutation Analysis, Yonsei Medical Journal, Jan. 1, 2012, pp. 132-137, vol. 53, No. 1, Yonsei University College of Medicine.

* cited by examiner

| stitching PCR set up | | #1 | #2 | final | | | #5 | #6 | final |
|---|---|---|---|---|---|---|---|---|---|
| MMx | 5X V11 MMx | 10 | 10 | 1x | 5X V11 MMx | | 10 | 10 | 1x |
| Mg | MgOAc 25mM | 6 | 6 | 3mM | MgOAc 25mM | | 6 | 6 | 3mM |
| primer | EX20 F (1uM) | | 5 | 100nM | EX20 F (1uM) | | | 5 | 100nM |
| primer | EX20 R01 (1uM) | | 5 | 100nM | EX20 R01 (1uM) | | | 5 | 100nM |
| template | pEGFR S268S (44 c/uL each) | 1 | 1 | 4x | pEGFR S268S (0.5 c/uL each) | | 1 | 1 | 0.05x |
| template | pEGFR T790T (44 c/uL each) | 1 | 1 | 4x | pEGFR T790T (0.5 c/uL each) | | 1 | 1 | 0.05x |
| | none | | | | none | | | | |
| SD | Sample Diluent | 32 | 22 | | Sample Diluent | | 32 | 22 | |
| | Total* | 50 | 50 | | Total* | | 50 | 50 | |
| Note | | templates only | templates plus flanking primers | | | | 10 fold more template | 10 fold templates plus flanking primers | |

FIG. 5

| Stitching PCR set up | | #1 | #2 | #3 | #4 | #5 | #6 | #7 | #8 | #9 | | final |
|---|---|---|---|---|---|---|---|---|---|---|---|---|
| MMx | 5X V11 MMx | 10 | 10 | 10 | 10 | 10 | 10 | 10 | 10 | 10 | | 1x |
| Mg | MgOAc 25mM | 6 | 6 | 6 | 6 | 6 | 6 | 6 | 6 | 6 | | 3mM |
| flanking primer | EXO2 F (1uM/10uM) | 5 | 5 | 5 | 5 | 5 | 5 | 5 | 10 | 2 | | 100/200/400nM |
| | EXO2 R01 (1uM/10uM) | 5 | 5 | 5 | | | | 5 | 10 | 2 | | 100/200/400nM |
| Stitching primer | EXO2 R11 (1uM) | | 2 | | 2 | | 2 | 5 | 5 | 5 | | 40/100nM |
| template | pEGFR 5280S (e5 c/uL each) | 1 | 1 | 1 | 1 | 1 | 1 | 1 | 1 | 1 | | e5 copy |
| | pEGFR T790T (e5c/uL each) | 1 | 1 | 1 | 1 | 1 | 1 | 1 | 1 | 1 | | e5 copy |
| | ddH2O | | | | | | | | | | | |
| SD | Sample Diluent | 22 | 20 | 17 | 20 | 17 | 18 | 12 | 2 | 18 | | |
| | Total* | 50 | 50 | 50 | 50 | 50 | 50 | 50 | 50 | 50 | | |
| Note | | PC | 1 stitch low conc pmr | 1 stitch regular conc pmr | 1 stitch low conc pmr | 1 stitch regular conc pmr | 2 stitch low conc pmr | 2 stitch regular conc pmr | 2 stitch high conc pmr 2:1 ratio | 2 stitch high conc pmr 4:1 ratio | | |

METHODS AND KITS FOR JOINING FRAGMENTED NUCLEIC ACIDS TOGETHER

FIELD OF THE INVENTION

The present disclosure relates to the field of nucleic acid amplification and in particular, to the joining fragmented pieces of nucleic acids.

BACKGROUND OF THE INVENTION

Extraction of DNA from formalin-fixed and paraffin-embedded (FFPE) tissue remains a challenge because formaldehyde, the effective component of formalin, leads to the generation of cross-linking between nucleic acids and proteins, and additionally causes nucleic acids to fragment because of fixation process conditions, e.g., the extremely low pH (Lin et al., Anal Biochem., 395(2): 265-267 (2009). Furthermore, the detection of circulating cell free DNA (cfDNA) and RNA in human blood, which has generated a lot of interest for its use in the so called liquid biopsy approach, has certain limitations, including the fragmented nature of such DNA with the average size being about 160 to 180 bp (Suzuki et al., Clinica Chimica Acta, 387, 55-58 (2008)).

For PCR based cancer diagnosis assays, the size limitation for fragmented DNA may not be a problem for mutation hot spots like BRAF V600, KRAS G12/G13, or PIK3CA E542/E545/E546 where the mutations duster in few nearby codons, but it is a challenge for others like EGFR exon 20 where mutations spread over 25 codons. The abundance of intact DNA in any sample may also be insufficient for accurate and sensitive detection of multiple mutation sites, so a method of target pre-enrichment before mutation detection is desirable. Methods for the pre-enrichment of target Nucleic Acids are known, but these methods involve multiple steps of reagent addition or are methods for the linear amplification of the target strands. The present disclosure addresses methods of such target pre-enrichment in an exponential and homogeneous manner without the need for multiple discrete steps and reagents. Therefore a method that can bring overlapping short nucleic acid fragments together and thus serve as the template for downstream PCR detection is desirable, which the present disclosure addresses.

SUMMARY OF THE INVENTION

In one embodiment, a method for joining fragmented nucleic acid together is provided, including performing an amplifying step including contacting a sample suspected of including a fragmented target nucleic acid with: a pair of external primers including a first nucleic acid sequence and a second nucleic acid sequence to produce a first amplification product including a first sense strand and a first anti-sense strand if any target nucleic acid is present in the sample; and a pair of internal primers complementary to each other including a third nucleic acid sequence and a fourth nucleic acid sequence, the third nucleic acid sequence configured to hybridize to the first antisense strand of the first amplification product to produce a second sense strand of a second amplification product and the fourth nucleic acid sequence configured to hybridize to the first sense strand of the first amplification product to produce a second anti-sense strand of the second amplification product; and generating a full length target nucleic acid by: annealing a first 3' end region of the first sense strand with a second 3' end region of the first anti-sense strand, wherein the first 3' end region of the first sense strand primes the extension of the first sense strand over the first anti-sense strand, and the second 3' end region of the first anti-sense strand primes the extension of the first anti-sense strand over the first sense strand; and annealing a third 3' end region of the second sense strand with a fourth 3' end region of the second anti-sense strand, wherein the third 3' end region of the second sense strand primes the extension of the second sense strand over the second anti-sense strand, and the fourth 3' end region of the second anti-sense strand primes the extension of the second anti-sense strand over the second sense strand.

In another embodiment, a kit for joining fragmented nucleic acid together is provided. The kit can include a pair of external primers including a first nucleic acid sequence and a second nucleic acid sequence to produce a first amplification product including a first sense strand and a first anti-sense strand if any of the target nucleic acid is present in the sample; and a pair of internal primers complementary to each other including a third nucleic acid sequence and a fourth nucleic acid sequence, the third nucleic acid sequence configured to hybridize to the first antisense strand of the first amplification product to produce a second sense strand of a second amplification product and the fourth nucleic acid sequence configured to hybridize to the first sense strand of the first amplification product to produce a second anti-sense strand of the second amplification product.

Unless otherwise defined, all technical and scientific terms used herein have the same meaning as commonly understood by one of ordinary skill in the art to which this invention belongs. Although methods and materials similar or equivalent to those described herein can be used in the practice or testing of the present subject matter, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION OF THE INVENTION

The present disclosure provides methods and kits for joining fragmented pieces of nucleic acids together, which is also referred to herein as "stitching" fragmented pieces of nucleic acids together. The disclosed methods and kits generate larger pieces of nucleic acid fragments by, e.g., bringing two overlapping short fragments to form a larger one, and also pre amplify the joined fragments to generate more templates for PCR amplification and detection.

Figure 1:
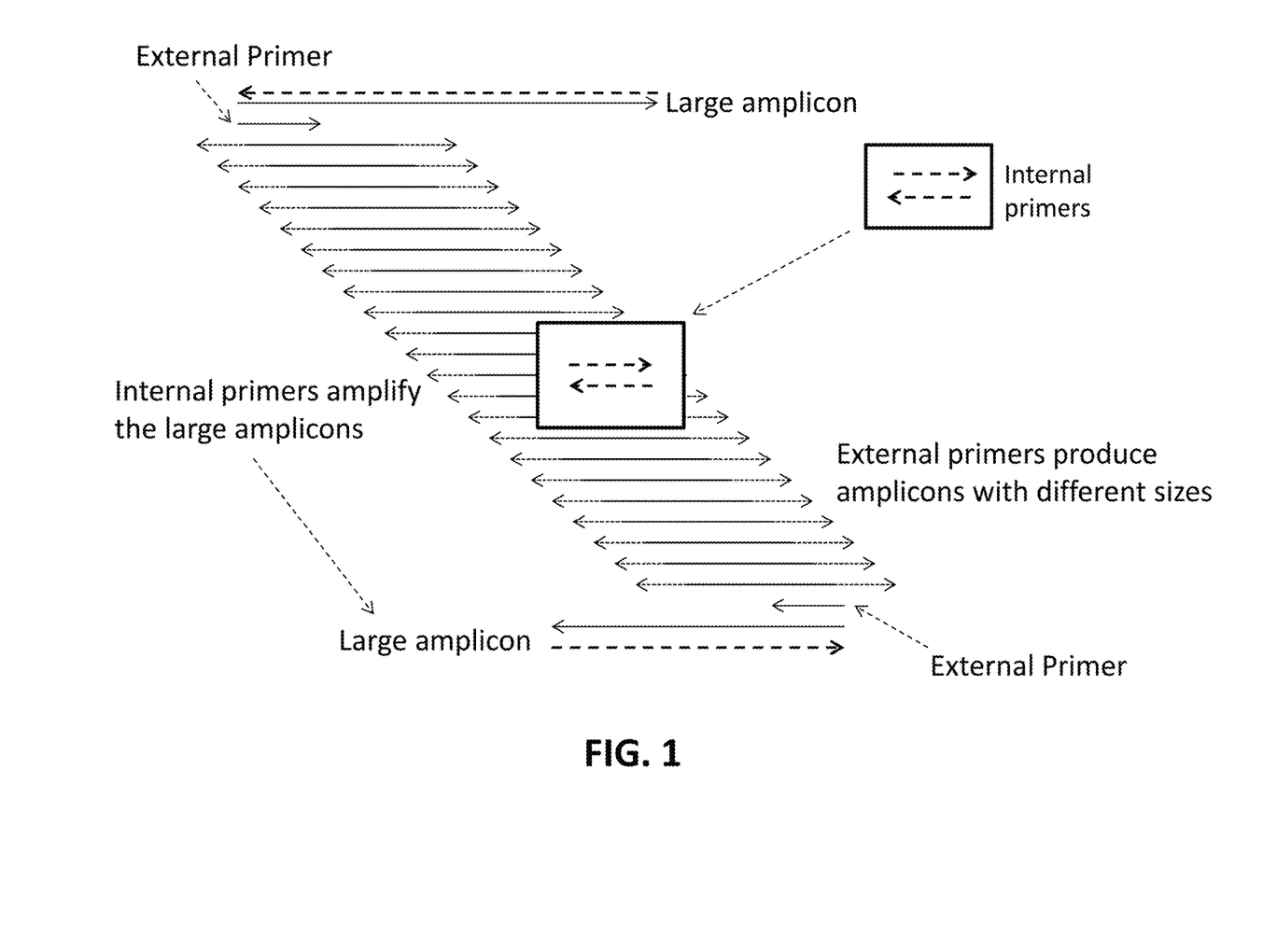
FIG. 1 shows a schematic diagram of utilization of a pair of external primers and a pair of internal primers complementary to each other to generate of various intermediate products.

The disclosed methods include steps for joining, or stitching, a fragmented piece of nucleic acid together to form the full length desired target nucleic acid target sequence. The disclosed methods include performing at least one cycling step that includes amplifying one or more portions of a fragmented target nucleic acid suspected of being present in a sample, using a pair of external primers and a pair of internal primers completely or substantially complementary to each other. The pair of external primers, together with the pair of internal primers complementary to each other, generates the full length target nucleic acid. The pair of external primers can include a first nucleic acid sequence and a second nucleic acid sequence to produce a first amplification product including a first sense strand and a first anti-sense strand if any target nucleic acid is present in the sample. The external primers may be capable but insufficient to generate a full length amplicon if the target nucleic acid is substantially fragmented or damaged. In a sample where a fragmented nucleic acid target is present, any one primer of the pair of external primers may produce a first amplification product derived from amplification with its partner external primer if the target DNA is intact, in such a way that primer binding sites are present within contiguous stretches of DNA from the sample. In the case where there are insufficient contiguous stretches of DNA in the sample to support amplification solely by the external primers, each of the external primers may participate in the generation of shorter second amplification products by the incorporation of one of the internal primers which are themselves complementary to internal regions of the desired first full length amplification product, if there is sufficient contiguous DNA between the external and internal primer binding sites. The two double stranded second amplification products generated from the two sets of external and corresponding internal primers, can be denatured by normal PCR thermal denaturation and the two amplicon single stands derived by extension of the external primers can hybridize with each other in such a way that the 3'-ends of these extension products can be extended to produce the full length target nucleic acid sequence (FIGS. 1, 2, and 3).

The pair of internal primers complementary to each other include a third nucleic acid sequence and a fourth nucleic acid sequence, wherein the third nucleic acid sequence is configured to hybridize to the first antisense strand of the first amplification product to produce a second sense strand of a second amplification product and the fourth nucleic acid sequence is configured to hybridize to the first sense strand of the first amplification product to produce a second anti-sense strand of the second amplification product. The pair of internal primers complementary to each other bind and extend both the existing (truncated) template sequences and the amplicons generated by the external primers. In a sample where a fragmented nucleic acid target is present, the pair of internal primers complementary to each other amplify the longer amplification products discussed above which can prime each other, thus increasing the production of the longer amplification products that are long enough to hybridize to each other and prime each other to produce the full length target nucleic acid sequence (FIGS. 1, 2, and 3). In one embodiment the relative concentration of the pair of internal primers complementary to each other is equal to the concentration of the pair of external primers. In another embodiment, the relative concentration of the pair of internal primers complementary to each other is lower than concentration of the pair of external primers.

In some embodiments, the disclosed methods may include a second, a third, or more pairs of internal primers complementary to each other. In each case the additional pair of internal primers complementary to each other can work together with the external primers or the adjacent pair of internal primers complementary to each other to produce one or more amplification products.

Figure 2:
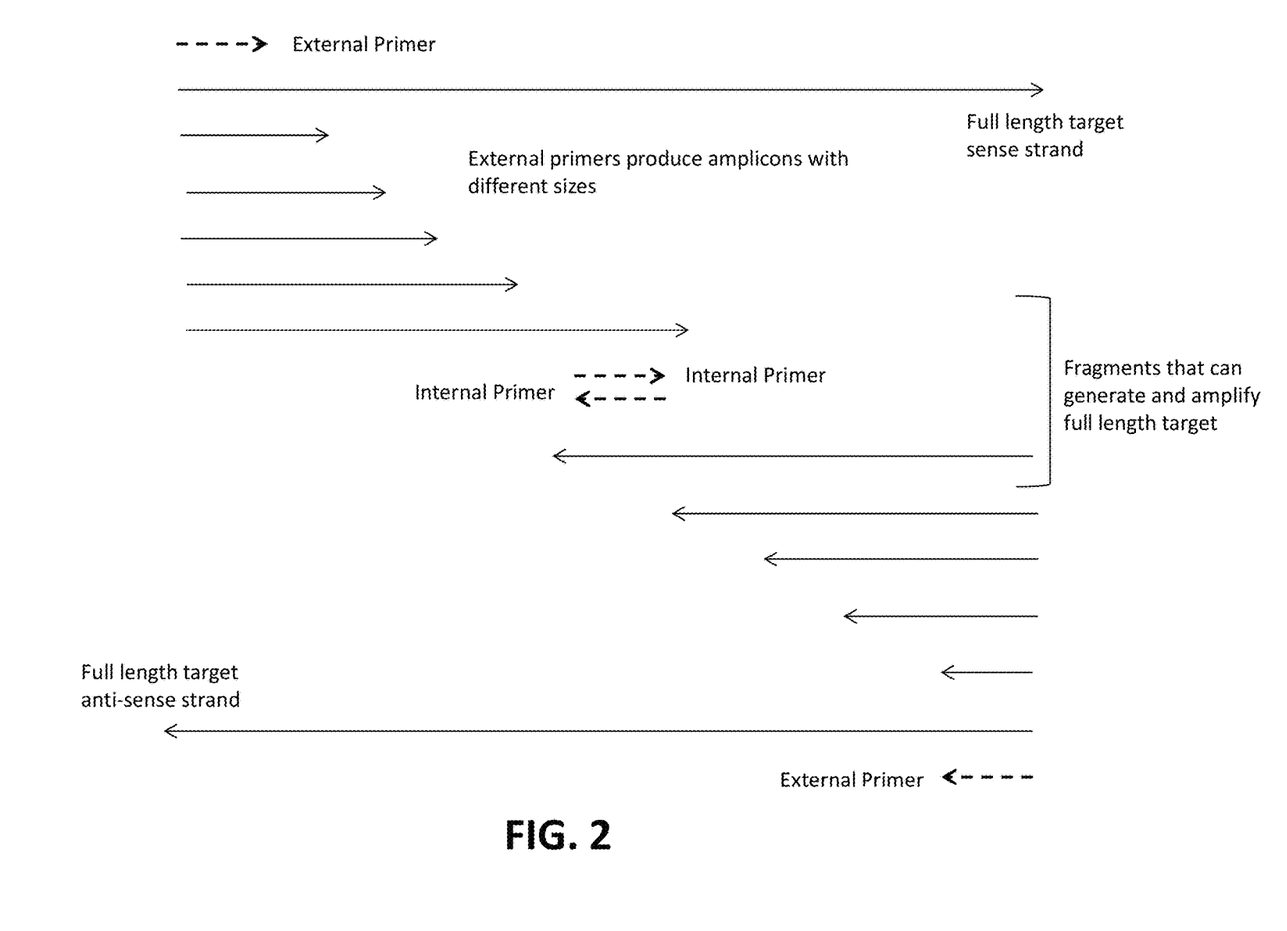
FIG. 2 shows a schematic diagram of utilization of a pair of external primers and a pair of internal primers complementary to each other to generate various intermediate products.
Figure 3:
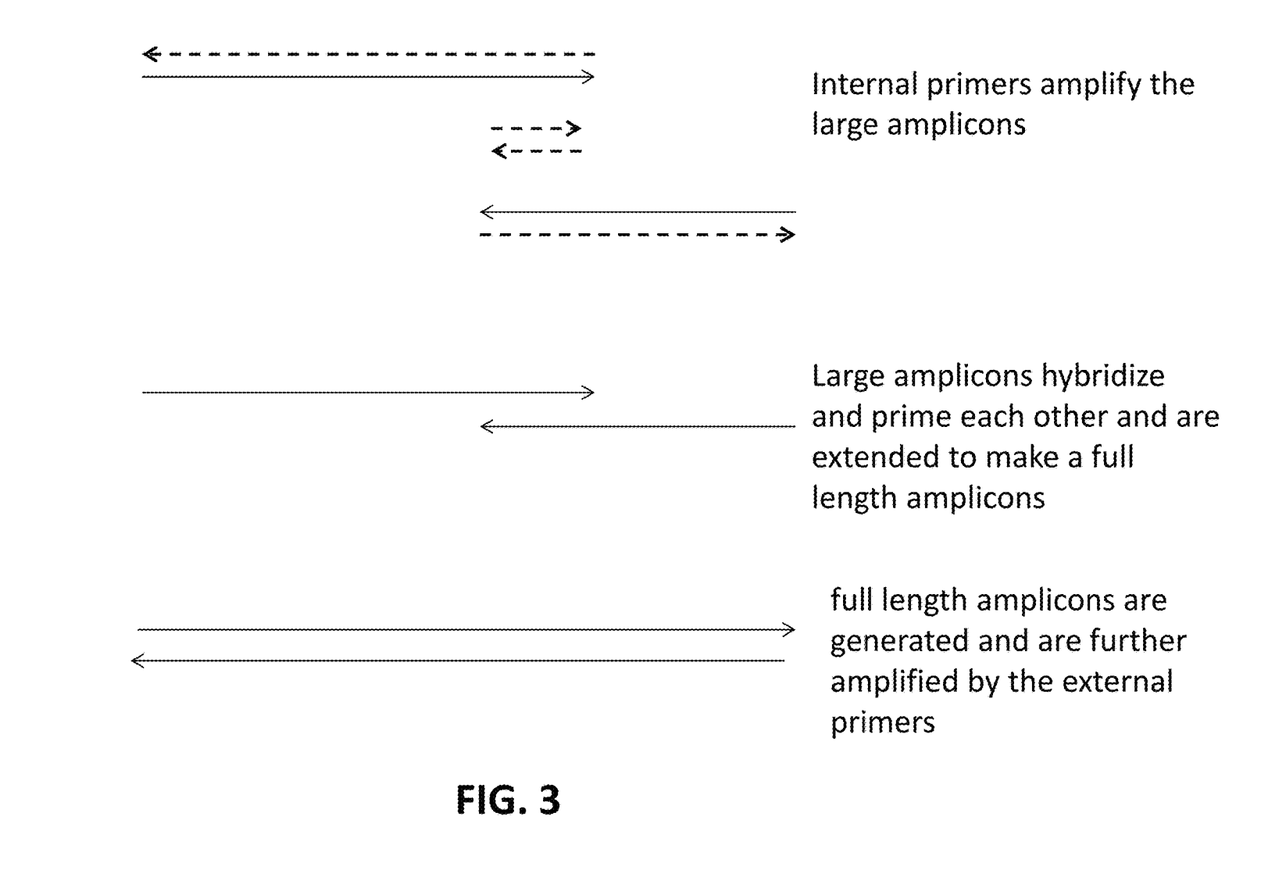
FIG. 3 shows a schematic diagram of utilization of a the amplification products produced by the pair of external primers and the pair of internal primers complementary to each other to generate the full length (stitched) product by the two intermediate products from the PCR reaction.

The disclosed methods include the step of generating a full length target nucleic acid, which can occur when the external primers have generated the first amplification products, including those of sufficient size wherein the sense and antisense strands of the first and second amplification products include regions which can hybridize together, thereby, each acting as a primer for the complementary strand (FIGS. 2 and 3). In this way, the full length target nucleic acid molecule can be produced and amplified by annealing a first 3' end region of the first sense strand with a second 3' end region of the first anti-sense strand, wherein the first 3' end region of the first sense strand primes the extension of the first sense strand over the first anti-sense strand, and the second 3' end region of the first anti-sense strand primes the extension of the first anti-sense strand over the first sense strand. In addition, the full length target nucleic acid can also be generated when the internal primers complementary to each other have generated the second amplification products of sufficient size are produced wherein the second sense and second antisense strands of the second amplification product include a region which can hybridize together, which can be the region represented by the internal primers complementary to each other, and each strand extended in the 5' direction to the region represented by the external primers, thereby, each acting as a primer for the complementary strand (FIGS. 2 and 3). In this way, the full length target nucleic acid molecule can be produced and amplified by annealing a third 3' end region of the second sense strand with a fourth 3' end region of the second anti-sense strand, wherein the third 3' end region of the second anti-sense strand primes the extension of the second sense strand over the second anti-sense strand, and the fourth 3' end region of the second anti-sense strand primes the extension of the second anti-sense strand over the second sense strand. As the amplification process continues and more of the larger fragments are produced leading to the production of greater and greater amount of the full length target nucleic acid molecule.

The term "sense strand" as used herein, refers to the strand of DNA that has the same sequence as the mRNA, which takes the antisense strand as its template during transcription. Other terms in the art that are synonymous to "sense strand" are "coding strand", "positive (+) strand", and "non-template strand".

The term "anti-sense strand" as used herein, refers to the non-coding DNA strand of a gene with bases complementary to the DNA sense strand and used as a template for the mRNA. Other terms in the art that are synonymous to "anti-sense strand" are "non-coding strand". "negative (−) strand", and "template strand".

"Primer(s)" as used herein refer to oligonucleotide primers that specifically anneal to nucleic acid sequence encoding a target of interest, and initiate DNA synthesis therefrom under appropriate conditions producing the respective amplification products. Each of the discussed primers can anneal to a target within or adjacent to the respective target nucleic acid molecule such that at least a portion of each amplification product contains nucleic acid sequence corresponding to the target. The amplification product should contain the nucleic acid sequences that are complementary to one or more detectable probes for the target of interest. "Probe(s)" as used herein refer to oligonucleotide probes that specifically anneal to nucleic acid sequence encoding the target of interest.

Each cycling step may include an amplification step, a hybridization step, and a detection step, in which the sample is contacted with the one or more detectable probes for detection of the presence or absence of the target of interest in the sample.

As used herein, the term "amplifying" refers to the process of synthesizing nucleic acid molecules that are complementary to one or both strands of a template nucleic acid molecule of interest. Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" as used herein is known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'-OH group whereto further "nucleotides" may be attached by a template-dependent DNA polymerase establishing 3' to 5' phosphodiester linkage whereby deoxynucleoside triphosphates are used and whereby pyrophosphate is released. Therefore, there is—except possibly for the intended function—no fundamental difference between a "primer", an "oligonucleotide", or a "probe".

The term "hybridizing" refers to the annealing of one or more probes to an amplification product. Hybridization conditions typically include a temperature that is below the melting temperature of the probes but that avoids non-specific hybridization of the probes.

The term "5' to 3' nuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. laceus, T. rubens, Bacillus stearothermophilus*, and *Methanothermus fervidus*. Nonetheless, polymerases that are not thermostable also can be employed in PCR assays provided the enzyme is replenished.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3 terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:31-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino dC, a C5 propargylamino-dU, a C7 propargylamino, dA, a C7 propargylamino-dG, a 7-deaza-2-deoxyxanthosine, a pyrazolopyrimidine analog, a pseudo-dU, a nitro pyrrole, a nitro indole, 2'-O-methyl Ribo-U, 2'-O-methyl Ribo-C, an N4-ethyl-dC, an N6-methyl-dA, and the like. Many other modified nucleotides that can be substituted in the oligonucleotides are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments. Examples of these types of nucleic acid modifications are described in, e.g., U.S. Pat. No. 6,001,611, which is incorporated herein by reference.

Detection of the Target Nucleic Acid Sequence

The present disclosure provides methods to detect the target nucleic acid sequence by amplifying, for example, a portion of the target nucleic acid sequence. Nucleic acid sequences of the target nucleic acid should be known with specificity. Specifically, primers and probes to amplify and detect target nucleic acid molecule targets are provided by the embodiments in the present disclosure.

For detection of the target nucleic acid sequence, primers and probes to amplify the can be provided, an in addition, functional variants can be evaluated for specificity and/or sensitivity by those of skill in the art using routine methods. Representative functional variants can include, e.g., one or more deletions, insertions, and/or substitutions in the target nucleic acids.

More specifically, embodiments of the oligonucleotides each include a nucleic acid with a sequence selected to perfectly match the target, or It may include a substantially identical variant thereof in which the variant has at least, e.g., 80%, 90%, or 95% sequence identity, or a complement of the variant.

In one embodiment, the above described sets of primers and probes are used in order to provide for detection of the target nucleic acid sequence in a biological sample suspected of containing the target. The sets of primers and probes may comprise or consist of the primers and probes specific for the target nucleic acid sequences, or, in another embodiment, the primers and probes for the target nucleic acid sequence may comprise or consist of a functionally active variant of any of the primers and probes.

A functionally active variant of any of the primers and/or probes may be identified by using the primers and/or probes in the disclosed methods. A functionally active variant of a primer and/or probe pertains to a primer and/or probe which provides a similar or higher specificity and sensitivity in the described method or kit as compared to the respective sequence.

The variant may, e.g., vary from the sequence by one or more nucleotide additions, deletions or substitutions such as one or more nucleotide additions, deletions or substitutions at the 5' end and/or the 3' end of the respective sequence. As detailed above, a primer (and/or probe) may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-desazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify a nucleic acid molecule encoding the target, e.g., nucleic acids encoding alternative portions of target nucleic acid sequence can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length).

In addition to a set of primers, the methods may use one or more probes in order to detect the presence or absence of the target nucleic acid sequence. The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids". A "probe" can be referred to as a "detection probe" meaning that it detects the target nucleic acid.

In some embodiments, the described probes can be labeled with at least one fluorescent label. In one embodiment, the probes can be labeled with a donor fluorescent moiety, e.g., a fluorescent dye, and a corresponding acceptor moiety, e.g., a quencher. In one embodiment, the probe comprises or consists of a fluorescent moiety and the nucleic acid sequences.

Designing oligonucleotides to be used as probes can be performed in a manner similar to the design of primers. Embodiments may use a single probe or a pair of probes for detection of the amplification product. Depending on the embodiment, the probe(s) use may comprise at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 40 (e.g., 16, 18, 20, 21, 22, 23, 24, or 25) nucleotides in length.

Constructs can include vectors each containing one of primers and probes nucleic acid molecules. Constructs can be used, for example, as control template nucleic acid molecules. Vectors suitable for use are commercially available and/or produced by recombinant nucleic acid technology methods routine in the art. Nucleic acid molecules can be obtained, for example, by chemical synthesis, direct cloning from the target, or by PCR amplification.

Constructs suitable for use in the methods typically include, in addition to the target nucleic acid molecules sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs containing target nucleic acid molecules can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens*, and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in some embodiments include oligonucleotides capable of acting as points of initiation of nucleic acid synthesis within the described target nucleic acid sequences. A primer can be purified from a restriction digest by conventional methods, or it can be produced synthetically. The primer is preferably single-stranded for maximum efficiency in amplification, but the primer can be double, stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence on the described target nucleic acid molecules. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

PCR assays can employ target nucleic acid such as RNA or DNA (cDNA). The template nucleic acid need not be purified; it may be a minor fraction of a complex mixture, such as target nucleic acid contained in human cells. Target nucleic acid molecules may be extracted from a biological sample by routine techniques such as those described in *Diagnostic Molecular Microbiology Principles and Applications* (Persing et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonucleotide primers are combined with PCR reagents under reaction conditions that induce primer extension. For example, chain extension reactions generally include 50 mM KCl, 10 mM Tris-HCl (pH 8.3), 15 mM $MgCl_2$, 0.001% (w/v) gelatin, 1.0 ng-1.0 µg denatured template DNA, 50 µmoles of each oligonucleotide primer, 2.5 U of Taq polymerase, and 1096 DMSO). The reactions usually contain 150 to 320 µM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acid molecules. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength. In certain systems, non-fluorescent energy can be transferred between donor and acceptor moieties, by way of biomolecules that include substantially non-fluorescent donor moieties (ace, for example, U.S. Pat. No. 7,741,467).

In one example, a oligonucleotide probe can contain a donor fluorescent moiety and a corresponding quencher, which may or not be fluorescent, and which dissipates the transferred energy in a form other than light. When the probe is intact, energy transfer typically occurs between the donor and acceptor moieties such that fluorescent emission from the donor fluorescent moiety is quenched the acceptor moiety. During an extension step of a polymerase chain reaction, a probe bound to an amplification product is cleaved by the 5' to 3' nuclease activity of, e.g., a Taq Polymerase such that the fluorescent emission of the donor fluorescent moiety is no longer quenched. Exemplary probes for this purpose are described in, e.g., U.S. Pat. Nos. 5,210,015, 5,994,056, and 6,171,785. Commonly used donor-acceptor pairs include the PAM-TAMRA pair. Commonly used quenchers are DABCYL and TAMRA. Commonly used dark quenchers include BlackHole Quenchers™ (BHQ), (Biosearch Technologies, Inc., Novato, Calif.), Iowa Black™, (Integrated DNA Tech., Inc., Coralville, Iowa), BlackBerry™ Quencher 650 (BBQ-650), (Berry & Assoc., Dexter, Mich.).

In another example, two oligonucleotide probes, each containing a fluorescent moiety, can hybridize to an amplification product at particular positions determined by the complementarity of the oligonucleotide probes to the target nucleic acid sequence. Upon hybridization of the oligonucleotide probes to the amplification product nucleic acid at the appropriate positions, a FRET signal is generated. Hybridization temperatures can range from about 35' C. to about 65' C. for about 10 sec to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorimeter. Excitation to initiate energy transfer, or to allow direct detection of a fluorophore, can be carried out with an argon ion laser, a high intensity mercury (Hg) arc lamp, a fiber optic light source, or other high intensity light source appropriately filtered for excitation in the desired range.

As used herein with respect to donor and corresponding acceptor moieties "corresponding" refers to an acceptor fluorescent moiety or a dark quencher having an absorbance spectrum that overlaps the emission spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Forster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothiocyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5. Lissamine rhodamine B sulfonyl chloride, tetramethyl rhodamine isothiocyanate, rhodamine x isothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm can be the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety, such as an LC Red 640, can be combined with an oligonucleotide which contains an amino linker (e.g., C6-amino phosphoramidites available from ABI (Poster City, Calif.) or Glen Research (Sterling, Va.)) to produce, for example, LC Red 640 labeled oligonucleotide. Frequently used linkers to couple a donor fluorescent moiety such as fluorescein to an oligonucleotide include thiourea linkers (FITC derived, for example, fluorescein-CPG's from Glen Research or ChemGene (Ashland, Mass.)), amide-linkers (fluorescein-NHS-ester-derived, such as CX-fluorescein-CPG from BioGenex (San Ramon, Calif.)), or 3'-amino-CPGs that require coupling of a fluorescein-NHS-ester after oligonucleotide synthesis.

Detection of the Target Nucleic Acid Molecule

The present disclosure provides methods for detecting the presence or absence of the target nucleic acid molecule in a biological or non-biological sample. Methods provided avoid problems of sample contamination, false negatives, and false positives. The methods include performing at least one cycling step that includes amplifying a portion of the target nucleic acid molecules from a sample using one or more pairs of primers, and a FRET detecting step. Multiple cycling steps are performed, preferably in a thermocycler. Methods can be performed using the primers and probes to detect the presence of the target, and the detection of target indicates the presence of target in the sample.

As described herein, amplification products can be detected using labeled hybridization probes that take advantage of FRET technology. One FRET format utilizes TaqMan® technology to detect the presence or absence of an amplification product, and hence, the presence or absence of the target nucleic acid molecule. TaqMan® technology utilizes one single-stranded hybridization probe labeled with, e.g., one fluorescent dye and one quencher, which may or may not be fluorescent. When a first fluorescent moiety is excited with light of a suitable wavelength, the absorbed energy is transferred to a second fluorescent moiety or a dark quencher according to the principles of FRET. The second moiety is generally a quencher molecule. During the annealing step of the PCR reaction, the labeled hybridization probe binds to the target DNA (i.e., the amplification product) and is degraded by the 5' to 3' nuclease activity of, e.g., the Taq Polymerase during the subsequent elongation phase. As a result, the fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems) uses TaqMan® technology, and is suitable for performing the methods described herein for detecting the presence or absence of the target nucleic acid molecule in the sample.

Molecular beacons in conjunction with FRET can also be used to detect the presence of an amplification product using the real-time PCR methods. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Another common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler® Instrument. During FRET, the fluorescein transfers its energy to an acceptor fluorescent moiety such as LightCycler®-Red 640 (LC Red 640) or LightCycler®-Red 705 (LC Red 705). The acceptor fluorescent moiety then emits light of a longer wavelength, which is detected by the optical detection system of the LightCycler® instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of target genomes). If amplification of the target nucleic acid occurs and an amplification product is produced, the step of hybridizing results in a detectable signal based upon FRET between the members of the pair of probes.

Generally, the presence of FRET indicates the presence of the target nucleic acid molecule in the sample, and the absence of FRET indicates the absence of the target nucleic acid molecule in the sample. Inadequate specimen collection, transportation delays, inappropriate transportation conditions, or use of certain collection swabs (calcium alginate or aluminum shaft) are all conditions that can affect the success and/or accuracy of a test result, however. Using the methods disclosed herein, detection of FRET within, e.g., 45 cycling steps is indicative of the presence of the target nucleic acid molecule.

Representative biological samples that can be used in practicing the methods include, but are not limited to respiratory specimens, fecal specimens, blood specimens, dermal swabs, nasal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release the target nucleic acid or in some cases, the biological sample can be contacted directly with the PCR reaction components and the appropriate oligonucleotides.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides.

By detecting the temperature at which signal is lost, the melting temperature of probes can be determined. Similarly, by detecting the temperature at which signal is generated, the annealing temperature of probes can be determined. The melting temperature(s) of the probes from the target amplification products can confirm the presence or absence of the target in the sample.

Within each thermocycler run, control samples can be cycled as well. Positive control samples can amplify target nucleic acid control template (other than described amplification products of target genes) using, for example, control primers and control probes. Positive control samples can also amplify, for example, a plasmid construct containing the target nucleic acid molecules. Such a plasmid control can be amplified internally (e.g., within the sample) or in a separate sample run side-by-side with the patients' samples using the same primers and probe as used for detection of the intended target. Such controls are indicators of the success or failure of the amplification, hybridization, and/or FRET reaction. Each thermocycler run can also include a negative control that, for example, lacks target template DNA. Negative control can measure contamination. This ensures that the system and reagents would not give rise to a false positive signal. Therefore, control reactions can readily determine, for example, the ability of primers to anneal with sequence-specificity and to initiate elongation, as well as the ability of probes to hybridize with sequence-specificity and for FRET to occur.

In an embodiment, the methods include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next.

Conventional PCR methods in conjunction with FRET technology can be used to practice the methods. In one embodiment, a LightCycler® instrument is used. The following patent applications describe real-time PCR as used in the LightCycler® technology: WO 97/46707, WO 97/46714, and WO 97/46712.

The LightCycler® can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

As an alternative to FRET, an amplification product can be detected using a double-stranded DNA binding dye such as a fluorescent DNA binding dye (e.g., SYBR® Green or SYBR® Gold (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

It is understood that the embodiments of the present disclosure are not limited by the configuration of one or more commercially available instruments.

Articles of Manufacture/Kits

Embodiments of the present disclosure further provide for articles of manufacture or kits to detect the target nucleic acid sequence. An article of manufacture can include primers and probes used to detect the gene target, together with suitable packaging materials. Representative primers and probes for detection of target nucleic acid sequence are capable of hybridizing to the target nucleic acid molecules. In addition, the kits may also include suitably packaged reagents and materials needed for DNA immobilization, hybridization, and detection, such solid supports, buffers, enzymes, and DNA standards. Methods of designing primers and probes are disclosed herein, and representative examples of primers and probes that amplify and hybridize to the target nucleic acid molecules are provided.

Articles of manufacture can also include one or more fluorescent moieties for labeling the probes or, alternatively, the probes supplied with the kit can be labeled. For example, an article of manufacture may include a donor and/or an acceptor fluorescent moiety for labeling the probes. Examples of suitable FRET donor fluorescent moieties and corresponding acceptor fluorescent moieties are provided above.

Articles of manufacture can also contain a package insert or package label having instructions thereon for using the primers and probes to detect the target nucleic acid sequence in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

Embodiments of the present disclosure will be further described in the following examples, which do not limit the scope of the invention described in the claims.

EXAMPLES

The following examples and figures are provided to aid the understanding of the subject matter, the true scope of which is set forth in the appended claims. It is understood that modifications can be made in the procedures set forth without departing from the spirit of the invention.

Example I

Figure 4:
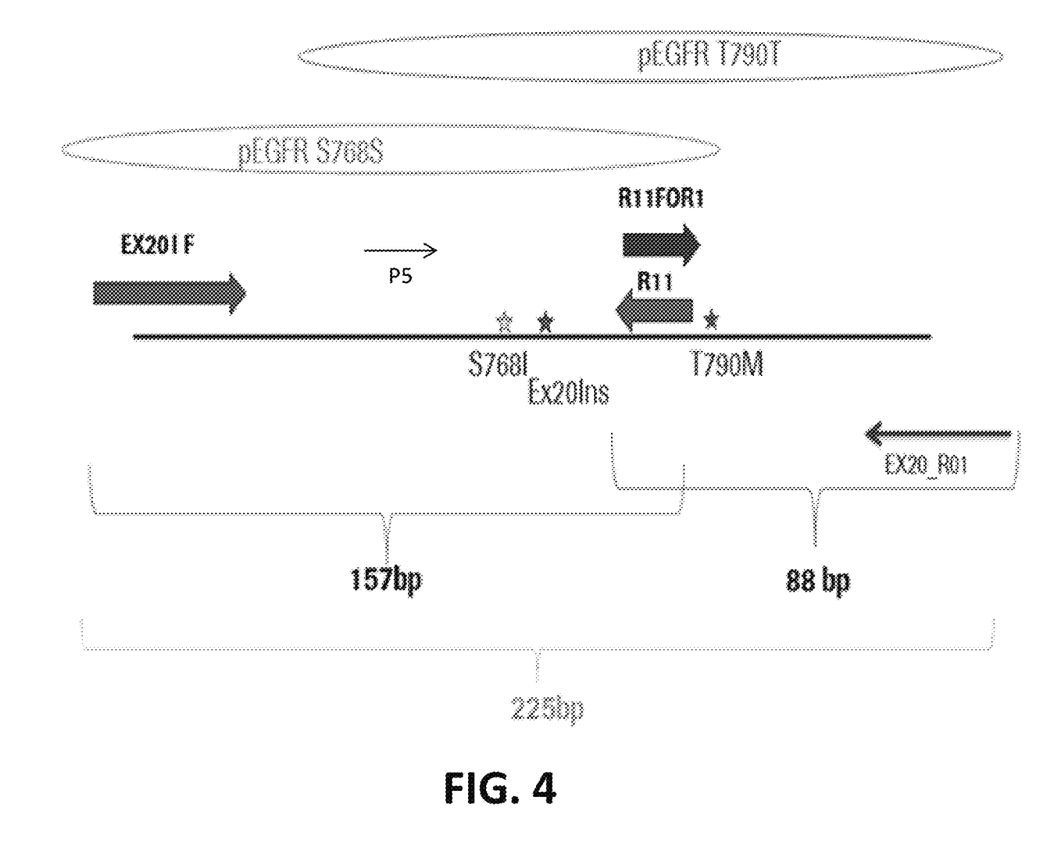
FIG. 4 shows a schematic diagram of EGFR exon 20 of and reagents used in the Example 1.

Referring to FIG. 4, there are three major mutations of EGFR exon20. In non-small cell lung cancer (NSCLC), T790M is a dominant resistant mutation which is detectable after first line treatment with Tyrosine Kinase Inhibitors. S768I and small insertions are found in many naïve NSCLC patients.

These 3 mutations are within a region of around 200-300 bp in the EGFR exon 20. The Nucleic Acids obtained from clinical samples from either plasma (cfDNA) or from FFPET are typically challenging to amplify and detect due to cross linking or from low natural abundance of full length target sequence. To enrich this full length target, two flanking (external) primers, EX20I F and EX20_R01 were initially used with a 500 bp minigene which gave successful results. However, the size of this amplicon, 225 bp, is not present in cell-free DNA (cfDNA) samples due to the size distribution of DNA in this sample type. Therefore joining of fragmented DNA (stitching) technique was applied to this must have target as a proof of concept.

Two 180 bp minigenes, pEGFR S768S and pEGFR T790T, were designed to mimic the fragmented cfDNA, two internal primers complementary to each other (stitching primers), R11FOR1 and R11, were designed to match a common sequence motif in each of the two minigenes. Simple PCRs using these primers were analyzed using gel analysis. Additionally, a TaqMan® probe, P5, was used to construct a qPCR assay with EX20I F and EX20_R01 used as the flanking (external) primers, this qPCR assay is used a sensitive method to detect the desired full length stitched product at 225 bp by real time PCR growth curve analysis.

Example II

Figure 5:
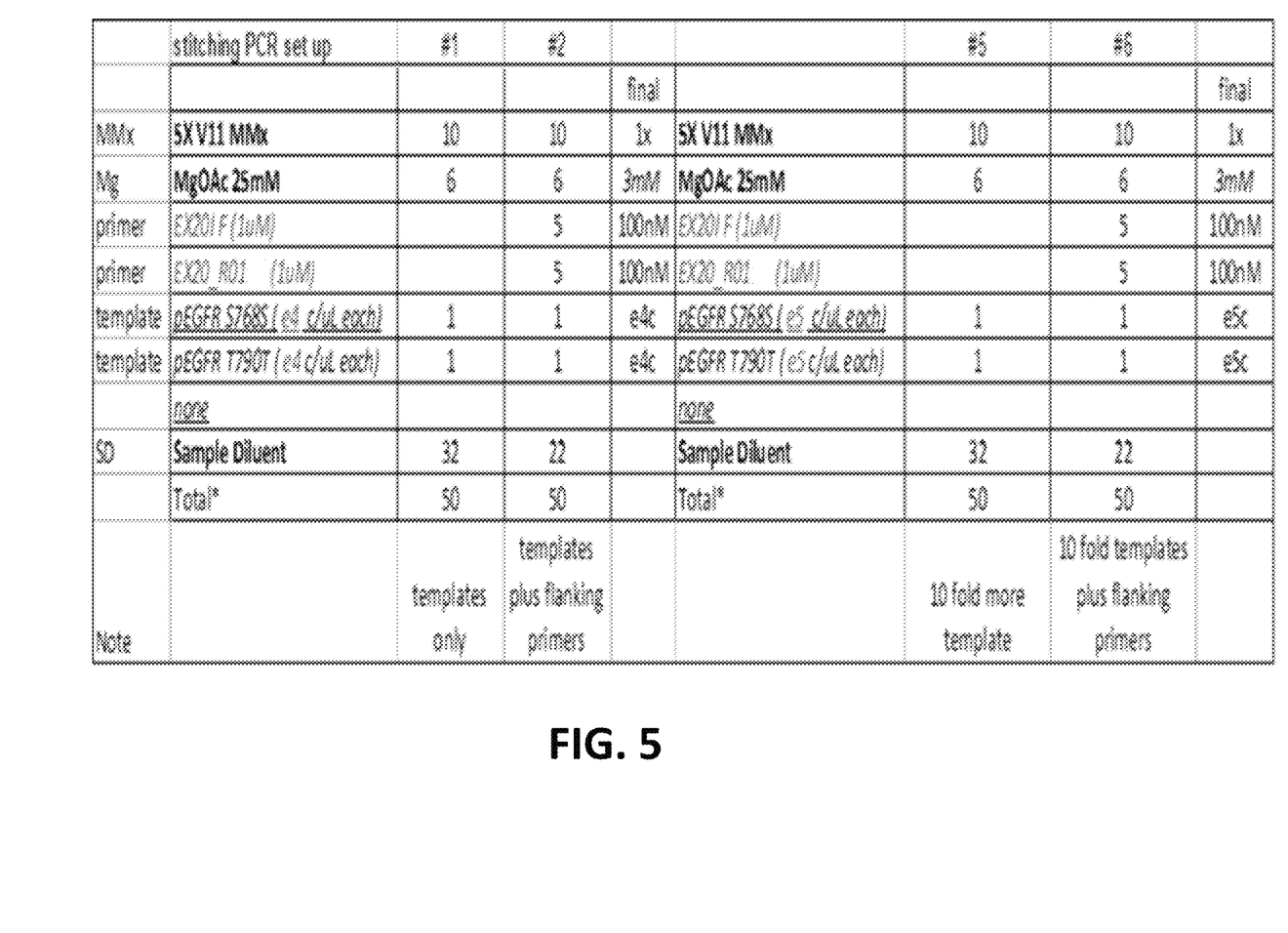
FIG. 5 shows a table of experimental design for various amounts of templates mixed with various amount of external primers.

Referring to FIG. 5, the table shows various amount of templates were mixed with various amount of flanking (external) primers. The goal was a successful and optimal reaction with two intermediate large amplicons (see FIG. 3). There were many attempts and different combinations tested to find out the best to generate the full length product.

The detection method was a qPCR TaqMan® assay which delivers sensitive and quantitative readout. One µL of the reactions described in FIG. 5 was used as the input for the qPCR Out of the four test conditions, only #6 gave good Ct. They are 17.7 for 35 cycles and 10.1 for 50 cycles. On a 4% agarose gel with 10 µL product loading, there is a faint band with the correct size at around 225 bp can be seen, though only for the 50 cycles reaction (data not shown). This positive result served as the base for the next experiment.

Example III

Figure 6:
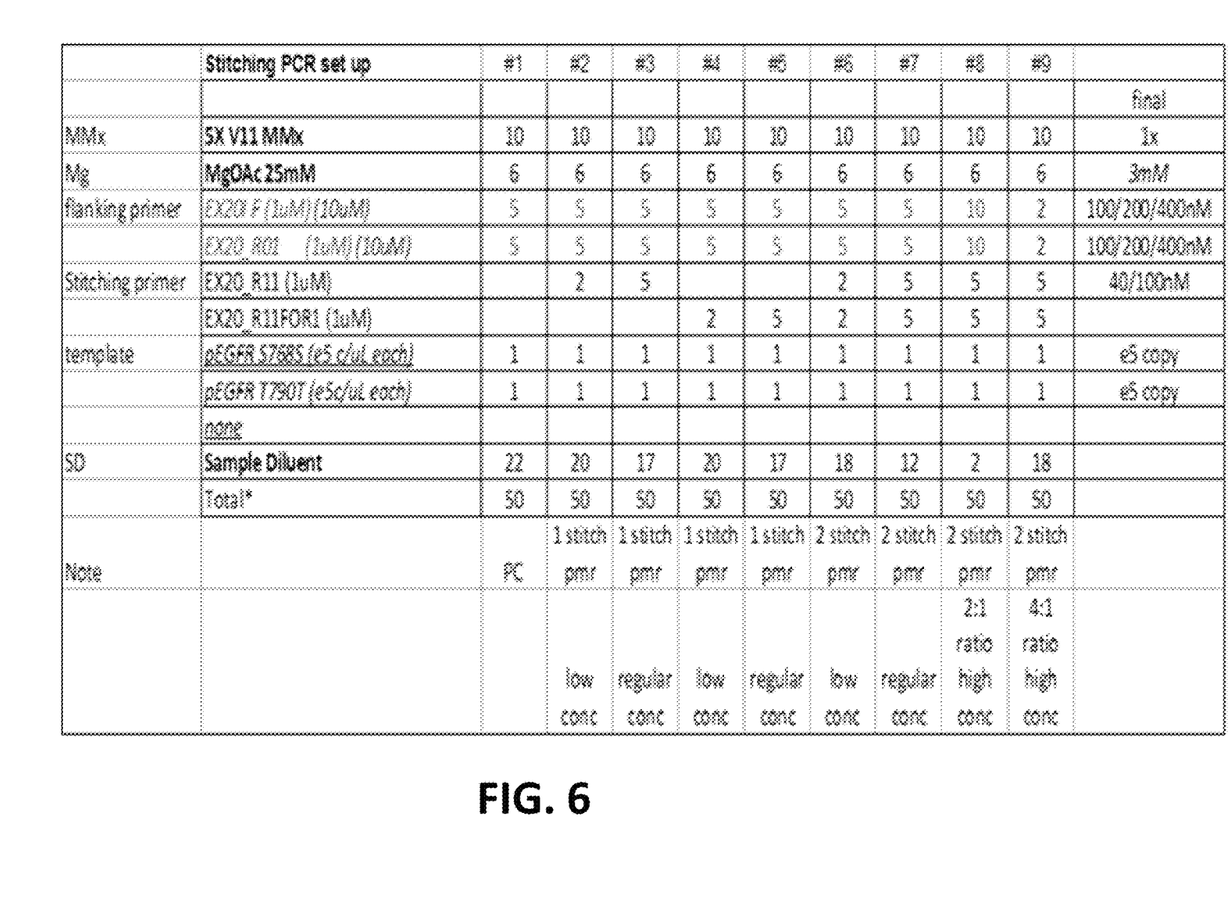
FIG. 6 shows a table of experimental design for titration of a wide range of internal primers complementary to each other (stitching primers) and external primers.

Referring to FIG. 6, the table shows an experiment designed to titrate a wide range of the internal primers complementary to each other (stitching primers).

1 is identical to the condition 46 described FIG. 5, serving as the positive control.

2 and #3 had one stitching primer, R11, added at two concentrations respectively. One was low at 40 nM and the other regular at 100 nM.

4 and #5 had the other stitching primer, R11FOR1, added at two concentrations respectively. One was low at 40 nM and the other regular at 100 nM.

6 to #9 had both stitching primers added with various concentrations combo together with the flanking primers. In #7 all four primers had the same regular concentration at 100 nM, while #8 and #9 had higher concentration for the flanking pair.

The reason for the different combinations is to test the boundary of this new method. Joining fragments of DNA (stitching) requires three different PCR reactions happening in the same tube in order to generate the final full length product.

Example IV

Figure 7:
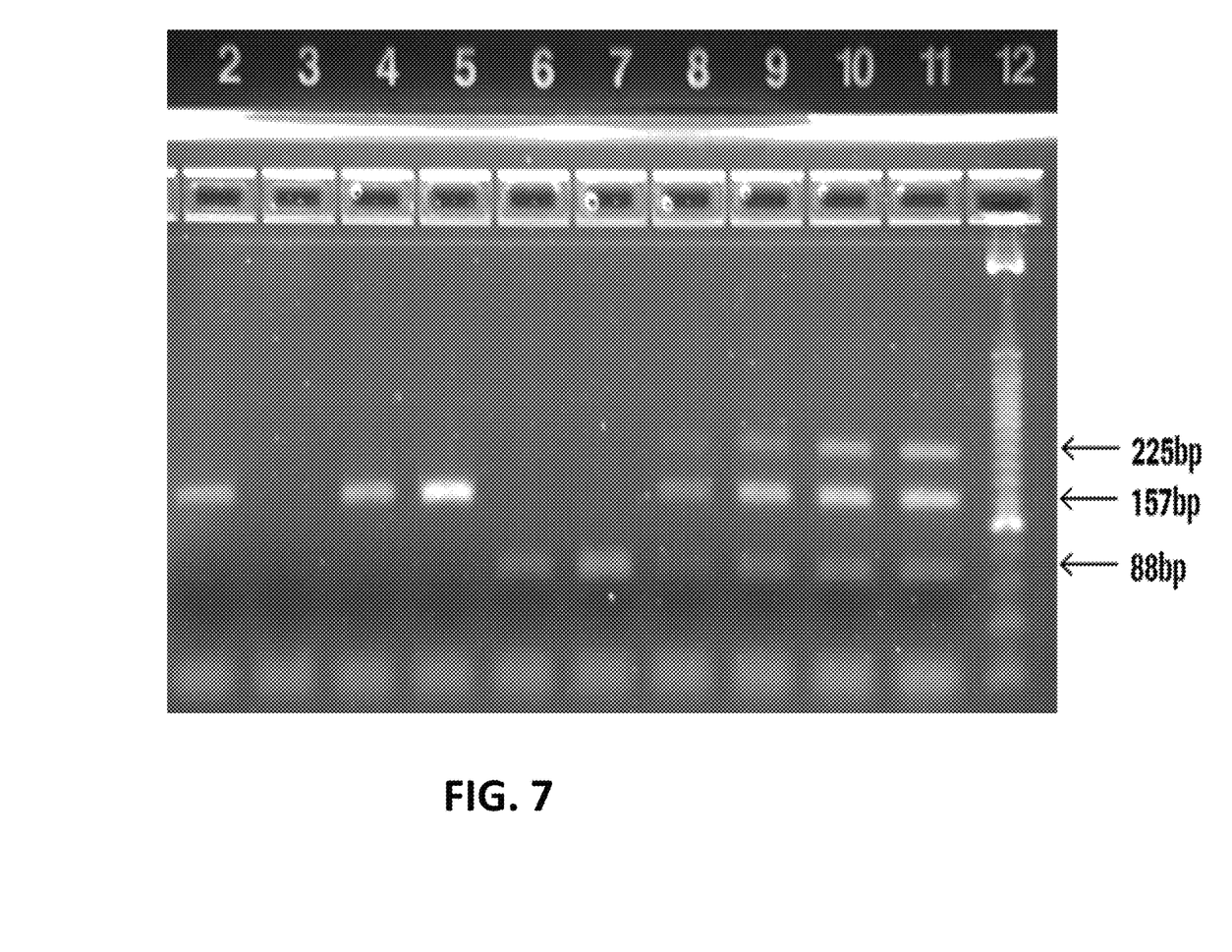
FIG. 7 shows an agarose gel including various PCR reactions based on experiments as shown in FIGS. 4-6.

Referring to FIG. 7 and Tables 1 and Table 2 below, two detection methods were used, qPCR and 4% agarose gel. One µL of 1:10 dilution of the reactions described in FIG. 6 was the input for the qPCR. The Ct value was shown below in Table 1.

TABLE 1

| #1 | #2 | #3 | #4 | #5 | #6 | #7 | #8 | #9 |
|---|---|---|---|---|---|---|---|---|
| 26.4 | 21.3 | 20.4 | 19.5 | 20.1 | 8* | 7* | 6* | 6* |

*Estimate due to early Ct call

6 to #9 clearly generated much more full length product than using one stitching primer conditions (#2 to #5). But qPCR in this case cannot differentiate products of different size, while agarose gel can (see FIG. 7, and Table 2).

TABLE 2

| well | stitch prm | conc | gel band |
|---|---|---|---|
| 3 | none | | Not seen |
| 4 | R11 | low | weak 157 bp |
| 5 | R11 | normal | strong 157 bp |
| 6 | R11FOR1 | low | weak 88 bp |
| 7 | R11FOR1 | normal | strong 88 bp |
| 8 | R11 + R11FOR1 | low | weak 225 bp |
| 9 | R11 + R11FOR1 | normal | weak plus 225 bp |
| 10 | R11 + R11FOR1 | high 2:1 | medium 225 bp |
| 11 | R11 + R11FOR1 | high 4:1 | medium 225 bp |
| 12 | | | 25 bp marker |

FIG. 7 shows an agarose gel includes various stitching reactions. 10 µL of the reactions described in FIG. 6 plus 10 µL loading dye was loaded in each well. Well 2: 157 bp size positive control; Well 3-11 are reaction #1-#9 described in FIG. 6 respectively; Well 12 is 25 bp marker by Invitrogen. The results are summarized below:

There is a clearly quantitative and dynamic aspect of the stitching reaction, as shown in FIG. 7. The Ct=26.4 in reaction #1/well 3, so clearly there are full length products present. But the concentration is around 32 fold lower than reaction #2 (Ct=21.3), that's why the band is not seen.

Reaction #2 and #3 (well 4 and 5): with the presence of two concentrations of R11, the 157 bp product is clearly seen with a dosage effect. But there is no full length product at 225 bp seen on the gel (Ct=21.3 and 20.4), Not much of the full length 225 bp product generated is presumably due to the concentration of the two required intermediate large amplicons are skewed and not within the optimal boundary.

Reaction #4 and #5 (well 6 and 7): with the presence of two concentrations of R11FOR1, the 88 bp product is clearly seen with a dosage effect. But there is no full length product seen on the gel either (Ct=19.5 and 23.1). It could be the same reason as above.

Reaction #6 to #9 (well 8-11): with the presence of both stitching primers in the same reaction, the full length product at 225 bp is clearly seen with a dosage effect. With a fixed flanking primer concentration, the more stitching primers the more full length (well 8 vs well 9). With a fixed stitching primer concentration, the more flanking primers doesn't seem to increase the full length product further (well 10 vs well 11), suggesting it reaches the plateau:

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A homogeneous method for joining fragmented nucleic acids together to produce a full-length target nucleic acid, comprising the steps of:
    a) performing an amplifying step comprising contacting a sample suspected of comprising fragmented target nucleic acids with:
        a pair of external primers comprising a first nucleic acid sequence and a second nucleic acid sequence to produce a first amplification product comprising a first sense strand and a first anti-sense strand if any fragmented target nucleic acids are present in the sample; and
        a pair of internal primers complementary to each other comprising a third nucleic acid sequence and a fourth nucleic acid sequence, the third nucleic acid sequence configured to hybridize to the first anti-sense strand of the first amplification product to produce a second sense strand of a second amplification product and the fourth nucleic acid sequence configured to hybridize to the first sense strand of the first amplification product to produce a second anti-sense strand of the second amplification product; and
    b) generating the full-length target nucleic acid by:
        i) annealing a first 3' end region of the first sense strand with a second 3' end region of the first anti-sense strand, wherein the first 3' end region of the first sense strand primes the extension of the first sense strand over the first anti-sense strand, and the second 3' end region of the first anti-sense strand primes the extension of the first anti-sense strand over the first sense strand; and
        ii) annealing a third 3' end region of the second sense strand with a fourth 3' end region of the second anti-sense strand, wherein the third 3' end region of the second sense strand primes the extension of the second sense strand over the second anti-sense strand, and the fourth 3' end region of the second anti-sense strand primes the extension of the second anti-sense strand over the second sense strand;
    wherein steps a) and b) and substeps i) and ii) are performed in a homogeneous manner; and
    wherein the sample suspected of comprising the fragmented target nucleic acids is a biological sample or a clinical sample, wherein the biological sample is selected from respiratory specimens, fecal specimens, blood specimens, dermal swabs, nasal swabs, wound swabs, blood cultures, skin, or soft tissue infections.

2. The method of claim 1, wherein the clinical sample is selected from formalin-fixed and paraffin-embedded tissue (FFPET), blood, or plasma.

3. The method of claim 1, further comprising the steps of:
    c) performing a hybridizing step comprising contacting the full-length target nucleic acid with one or more detectable probes; and
    d) detecting the presence or absence of the full-length, target nucleic acid;
wherein steps a), b), substeps i) and ii), and steps c) and d) are all performed in a homogenous manner.

4. The method of claim 3, wherein:
    the hybridizing step c) comprises contacting the full-length target nucleic acid with one of the one or more detectable probes comprising a labeled nucleic acid sequence that has a donor fluorescent moiety and a corresponding acceptor moiety; and
    the detecting step d) comprises detecting the presence or absence of fluorescence resonance energy transfer (FRET) between the donor fluorescent moiety and the acceptor moiety of the labeled nucleic acid sequence, wherein the presence or absence of fluorescence is indicative of the presence or absence of the full-length target nucleic acid.

5. The method of claim 3, wherein the hybridizing step c) comprises contacting the full-length target nucleic acid with one of the one or more detectable probes comprising a molecular probe comprising a double-stranded DNA binding dye that upon interaction with a double-stranded nucleic acid of the full-length target nucleic acid emits a fluorescence signal; and the detecting step d) comprises detecting the presence or absence of fluorescence resonance by a melting curve analysis, wherein the presence or absence of fluorescence is indicative of the presence or absence of the full-length target nucleic acid.

6. The method of claim 1, wherein relative concentration of the pair of internal primers complementary to each other is equal to or lower than the concentration of the pair of external primers.

7. The method of claim 1, wherein the amplifying step a) further comprises contacting the sample suspected of comprising fragmented target nucleic acids with a second pair of internal primers complementary to each other.

* * * * *